United States Patent
Mariotti et al.

(10) Patent No.: US 7,049,434 B2
(45) Date of Patent: May 23, 2006

(54) DERIVATIVES OF HYALURONAN

(75) Inventors: Paolo Mariotti, Cervignano del Friuli (IT); Luciano Navarini, Trieste (IT); Luca Stucchi, Pavia di Udine (IT); Vladimir Vinkovic, Zagreb (HR); Vitomir Šunjić, Zagreb (HR)

(73) Assignee: Eurand Pharmaceuticals Ltd. (IE)

( * ) Notice: Subject to any disclaimer, the term of this patent is extended or adjusted under 35 U.S.C. 154(b) by 14 days.

(21) Appl. No.: 10/479,529

(22) PCT Filed: Jun. 3, 2002

(86) PCT No.: PCT/EP02/06051

§ 371 (c)(1),
(2), (4) Date: Dec. 3, 2003

(87) PCT Pub. No.: WO02/098923

PCT Pub. Date: Dec. 12, 2002

(65) Prior Publication Data

US 2004/0157795 A1    Aug. 12, 2004

(30) Foreign Application Priority Data

Jun. 4, 2001 (IT) .......................... TS2001A0013

(51) Int. Cl.
*C08B 37/08* (2006.01)
*A61K 31/728* (2006.01)

(52) U.S. Cl. .................. 536/55.2; 536/55.3; 536/54; 536/123.1; 536/124; 514/54

(58) Field of Classification Search ............... 514/54; 536/53, 55.2, 55.3, 123.1, 124
See application file for complete search history.

(56) References Cited

U.S. PATENT DOCUMENTS

| | | | |
|---|---|---|---|
| 4,937,270 A | 6/1990 | Hamilton et al. | |
| 5,679,657 A | 10/1997 | Oka et al. | |
| 6,051,701 A * | 4/2000 | Cialdi et al. | 536/123 |
| 6,140,313 A | 10/2000 | Perbellini et al. | |
| 6,482,941 B1 | 11/2002 | Khan Riaz et al. | |

FOREIGN PATENT DOCUMENTS

| | | | |
|---|---|---|---|
| EP | 0216453 | 3/1996 | |
| JP | 54036388 | 3/1979 | |
| WO | 98/23648 | 6/1998 | |
| WO | 99/18133 | 4/1999 | |
| WO | WO 0001733 | * 1/2000 | |

OTHER PUBLICATIONS

T.C. Laurent et al., "Fractionation of Hyaluronic Acid—The Polydispersity of Hyaluronic Acid from the Bovine Vitreous Body," Biochim. Biophys. Acta, 42, pp. 476-485 (1960).

R. Khan et al., "Selective acetylation reactions of hyaluronic acid benzyl ester derivative," Carbohydrate Research 306, pp. 137-146 (1998).

* cited by examiner

*Primary Examiner*—James O. Wilson
*Assistant Examiner*—Ganapathy Krishnan
(74) *Attorney, Agent, or Firm*—Thompson Hine LLP

(57) ABSTRACT

The invention describes new hyaluronan derivatives where the hydroxyl groups are esterified or carbamoylated in amounts ranging from 0.01% to 100% and the carboxyl groups are either totally or partially esterified with alcohols or are in the form of salt.

20 Claims, 1 Drawing Sheet

DERIVATIVES OF HYALURONAN

FIELD OF THE INVENTION

The object of this invention concerns hyaluronan derivatives. These new compounds show specific physico-chemical features that make them suitable for several purposes. They can be useful, for example, as chiral selectors in chromatographic columns for the separation of enantiomers.

STATE OF THE ART

Hyaluronan, hereinafter HA, is an important component of a wide class of natural biopolymers that are also known as glycosaminoglycans (GAGs). These polymers in varying ratios with collagens and glycoproteins determine the structure and function of the extracellular matrix in animal tissues and organs. Their weight average molecular weight ranges from 1 to 10 millions in most tissues. Hyaluronan is composed of a disaccharidic repeating unit N-acetylhyalobiuronic acid consisting of repeating units of D-glucuronic acid and 2-acetamido-2-deoxy-D-glucose (N-acetylglucosamine) bound by a β(1→3) glycosidic link. Each repeating unit is bound to the next one by a β(1→4) glycosidic link that forms a linear polymer. The number of said repeating units in a polymer can get to several thousands and produce a chain of several thousands dalton. The term "hyaluronan" is commonly used to describe a general group of molecular fractions of HA with varying molecular weights or also hydrolised fractions of said compound. HA is present in higher organisms, it can be extracted from animal sources (for example rooster combs, humbilical chord, microbial sources (as for example some bacteria such as *Streptococcus* and *Pasteurella*).

HA plays an important role in several biological processes among which cellular motility and cell-to-cell interactions, in addition to its structural role deriving from its lubrifying and hydrating properties. Because of these biological properties, attention has always focussed on the biomedical applications of this polymer. As a consequence, HA has been widely used in viscosupplementation and viscosurgery, and in particular in the treatment of arthropathies and ophtalmic surgery wherein unmodified HA is used in the form of aqueous gel.

A different use of hyaluronan has been devised, that is in affinity chromatography for the separation of proteins of the cartilage. These proteins are separated from the other components by means of a specific biological binding with said polymer. This use is based on the biological activity of this polymer, that is the strong interaction hyaluronan-protein. This is the only known use of unmodified hyaluronan different from the biomedical application. However, this use is also linked to the biological properties of HA since it exploits the specific interaction of HA with the protein. On the contrary, nothing is known on the interaction of this polymer with substrates other than the biological ones, such as apolar and lipophylic substrates.

Chemical derivatives of HA have been widely studied with the aim of keeping the biocompatibility of the molecule and obtaining polymers that can be processed in manufacts or items such as tubes, stents, membranes, sponges, threads, surgical devices for implants. Literature describes two general approaches for the chemical modification of HA: (a) HA crosslinking by means of bifunctional chemical reagents and (b) modification of HA with monofunctional reagents. The latter approach resorts to the presence of three reactive groups present (acetamido, carboxyl, hydroxyl groups) on HA. The major effort was directed to the chemical modifications of the carboxyl and hydroxyl functions. The esterification reactions on the carboxyl groups of HA are described in EP 216453 that illustrates the either total or partial esterification of the carboxyl groups of HA with monofunctional organic halides for the production of materials with interesting properties and for use in cosmetics, surgery or medicine. The amidation reactions of HA are described in U.S. Pat. No. 4,937,270 that refers to a method for the preparation of biocompatible water insoluble gel.

As far as the hydroxyl groups of HA are concerned, several esterification reactions are described in literature. U.S. Pat. No. 5,679,657 describes the sodium salt of HA wherein 2.6–3.6 hydroxyl groups for each disaccharidic repeating unit were converted in acetyl groups. This product is soluble in 90% (w/w) water/ethanol mixtures and was tested for its smoothing properties. They are soluble in 90% (w/w) water/ethanol mixtures. The ester with butyric acid of hyaluronan salts has also been reported in the state of the art (WO98/23648) as an antiproliferative agent.

As far as the the total esterification of both HA carboxyls and hydroxyl groups is concerned, only one bibliographic reference (Khan et al., Carbohydrate Research (1998) 306, 137–146) describes the preparation of the totally acetylated derivative of HA benzylester (benzylester of acetylated hyaluronan) there are no further details on its properties and its possible uses.

The purpose of all the studies on the chemical modification of HA so far carried out was related to the preparation of new derivatives of HA that keep the native biocompatibility properties and to the preparation of new biomaterials or new drug release systems useful for the production of commercial manufacts. So far, all the major efforts to prepare chemically modified hyaluronan have focussed only on the biomedical applications; this polymer has not been derivatized yet for non-biocompatible applications.

DESCRIPTION OF THE INVENTION

Figure 1:
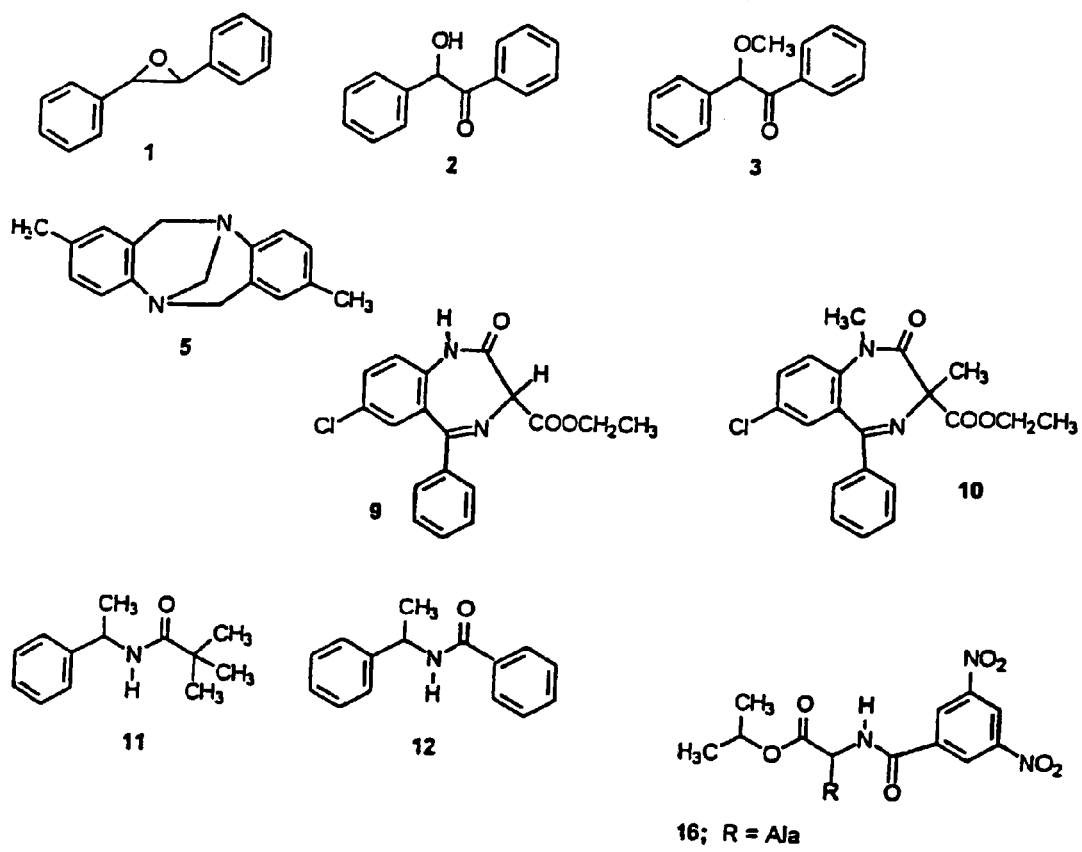
FIG. 1: list of the racemates tested

The invention describes new hyaluronan derivatives where the hydroxyl groups are esterified or carbamoylated in amounts ranging from 0.01% to 100% and the carboxyl groups are either totally or partially esterified with alcohols or are in the form of salt.

The hydroxyl groups are esterified with linear or branched, saturated or unsaturated aliphatic acids and have up to 24 carbon atoms; with cycloaliphatic or aliphatic cycloaliphatic acids, either mono- or polycyclic having up to 34 carbon atoms; with arylaliphatic acids wherein the aliphatic chain has 1–4 carbon atoms and the aryl residue can possibly be substituted with linear or branched C1–C5 alkyls, halogens, nitro groups, cyano groups, hydroxyl groups, amino groups, methoxy groups; with aryl acids wherein the aryl residue can possibly be substituted with linear or branched C1–C5 alkyls, halogens, nitro groups, cyano groups, hydroxyl groups, methoxy groups; with inorganic acids; with aromatic or non aromatic heterocyclic acids, possibly condensed with aromatic or non aromatic rings, wherein the heterocyclic group has 3–20 carbon atoms and can possibly be substituted with linear or branched C1–C5 alkyls, halogens, nitro groups, cyano groups, hydroxyl groups, amino groups, methoxy groups; with inorganic acids. Examples of esters obtained by esterification of the hydroxyl groups with aliphatic acids are: acetate, butyrate, propionate, retinoate, n-propylacetate. Examples of esters obtained by esterification of the hydroxyl groups with cycloaliphatic or aliphatic cycloaliphatic acids are: cyclohexanecarboxylate, cyclohexaneacetylate, cyclopropanecarboxylate. Examples of esters obtained by esterification of the hydroxyl groups with arylaliphatic acids are: phenylacetate, phenoxyacetate, naphtylacetate, 2-(4-isobutylphenyl)propionate, 2-(6-methoxy-2-naphtyl) propionate, cinnamate. Examples of esters obtained by esterification of the hydroxyl groups with arylic acids are: benzoate, substituted benzoate such as: halobenzoate, alchilbenzoate, nitrobenzoate, 2-acetoxybenzoate. Examples of esters obtained by esterification of the hydroxyl groups with inorganic acids are: nitrate. Examples of esters obtained by esterification of the hydroxyl groups with heterocyclic acids are: cinchonic acid, quinic acid, proline, nicotinic acid, meconic acid.

As an alternative to esterification, the hydroxyl groups can be carbamoylated with alkyl, alkylaryl, aryl isocyanates possibly substituted wherein the either linear or branched alkyl residue, satured or unsatured, has 2–6 carbon atoms and the aryl residue is a mono- or polynuclear residue, possibly substituted with linear or branched C1–C5 alkyls, halo groups, nitro groups, cyano groups, methoxy groups. Examples of carbamoylates are: halopbenylcarbamoylates, alkylphenylcarbamoylates, dialkylphenylcarbamoylates, dihalophenylcarbamoylates, halo-alkylphenylcarbamoylates, trialkylphenylcarbamoylates, methylphenylcarbamoylates, cyclohexylcarbamoylates, tert-butylcarbamoylates, 1-phenylethylcarbamoylates, benzylcarbamoylates.In these derivatives of the invention, all the hydroxyl groups, both the primary and the secondary, can be either esterified or carbamoylated in the same way, or else the primary groups can either be esterified or carbamoylated in a different way from the secondary hydroxyl groups.

In the derivatives of the invention, the carboxyl groups of hyaluronan are either totally or partially esterified with alcohols or they are in the salt form. The alcohols suitable for esterification are aliphatic, arylaliphatic, aryl, cycloaliphatic, heterocyclic alcohols. Aliphatic alcohols are linear or branched alcohols with up to 34 carbon atoms, they can be saturated or unsaturated, possibly substituted with halogens, nitro groups, cyano groups, hydroxyl groups, amino groups, methoxy groups. Examples are methylalcohol, ethylalcohol, propylalcohol. Alcohols containing benzene residues possibly substituted with 1–6 carbon atoms alkyl chains, with halogens, with hydroxyl groups, with amino groups belong to the arylaliphatic alcohols. Examples are benzyl alcohol, phenylethyl alcohol. The cycloaliphatic alcohols include also the aliphatic-cycloaliphatic alcohols, they can be either mono- or polycyclic, and have up to 34 carbon atoms. The heterocyclic alcohols can contain heteroatoms selected in the group consisting of O, S, N; they can be either aromatic or non aromatic, be possibly condensed with either aromatic or non aromatic rings and possibly substituted with linear or branched C1–C5 alkyls, halogens, nitro groups, cyano groups, hydroxyl groups, amino groups, methoxy groups. Examples are: tocopherol, quercetin.

The degree of substitution of the hydroxyl groups is expressed as the percentage (%) of either esterified hydroxyl groups or carbamoylated groups. The degree of substitution of the derivatives of the invention ranges from 0.01 to 100%. Two preferred substitution ranges of the hydroxyl groups are 0.01–0.2% and 70–100%.

The carboxyl groups of the derivatives of the invention are either totally or partially esterified with alcohols or they are in the form of salt. The degree of esterification of the carboxyl groups is expressed as the percentage (%) of carboxyl groups modified with alcohol. The degree of esterification is 100% when all carboxyl groups are esterified. When they are either partially esterified, then the non esterified groups are salified with alkaline metal cations, earth alkaline metal cations, nitrogen-containing cations. The nitrogen-containing cations include those containing organic nitrogen, such as the tetralkylammonium salts, wherein the alkyl has 1–5 carbon atoms. Other examples are lutidinium, collidinium., imidazolium salts. When the derivatives are partially esterified, then the preferred degree of esterification is higher than 50%.

The preferred hyaluronan derivatives of the invention belongs to the following groups:
first group: hyaluronan derivatives wherein the hydroxyl groups are esterified or carbamoylated in amounts ranging from 0.01% to 0.2% and the carboxyl groups are totally esterified (100% degree of esterification);
second group: hyaluronan derivatives wherein the hydroxyl groups are either esterified or carbamoylated in amounts ranging from 70% to 100% and the carboxyl groups are totally esterified (100% degree of esterification);
third group: hyaluronan derivatives wherein the hydroxyl groups are esterified or carbamoylated in amounts ranging from 70% to 100% and the carboxylic groups are in the salt form.

The preferred compounds belonging, as far as the substitution and esterification degree is concerned, to one of the above groups have the hydroxyl groups esterified with linear or branched, saturated or unsaturated aliphatic acids; with arylaliphatic acids; with arylic acids; or they have the hydroxyl groups carbamoylated with alkylaryl or arylisocyanates possibly substituted; these compounds have the carboxyl groups either partially or totally esterified with aliphatic, arylaliphatic, aryl alcohols or the carboxyl groups are in the form of nitrogen-containing cations. The preferred derivatives are tetrabutylammonium phenylcarbamoylated hyaluronan, benzylester of phenylcarbamoylated hyaluronan, benzylester of benzoate hyaluronan, methylester of butyrated hyaluronan, methylester of phenylcarbamoylated hyaluronan, methylester of phenylacetate hyaluronan, methylester of benzoate hyaluronan, allylester of phenylcarbamoylated hyaluronan, benzylester of butyrated hyaluronan, benzylester of phenylacetate hyaluronan, benzylester of 3,5-dimethylphenylcarbamoylated hyaluronan, methylester of 3,5-dimethylphenylcarbamoylated hyaluronan.

One further object of the invention is the preparation process of the derivatives. The process comprises the following steps:
a) possible either total or partial esterification of the carboxyl groups present on hyaluronan;
b) esterification or carbamoylation of the hydroxyl groups present on hyaluronan; wherein steps a) and b) can be applied in whatever order.

Step a) is carried out by mixing hyaluronan in its acid or salt form with a suitable halide in the presence of an organic solvent according to chemical conventional methods. The reaction is carried out preferably in N,N-dimethylformamide, at a temperature range from 2 to 40° C. for a time period ranging from 10 to 60-hours. The preferred starting material is hyaluronan in the salt form of quaternary ammonium. With variations in the reaction conditions as described in the state of the art, it is possible to obtain compounds with a different degree of esterification. Step b) may comprise several steps that allow the esterification or the carbamoylation of the hydroxyl groups. Step b) is carried out in a single step when the esterified or carbamoylated hydroxyls are both the primary hydroxyls and the secondary ones. The reaction is carried out by adding the suitable reagent either to the product obtained from step a) or to hyaluronran, either in the form of acid or salt, in organic solvents. The preferred solvents are the aprotic solvents such as dialkylsulfoxides, dialkylcarboxyamides, in particular C1–C6 dialkylsulfoxides, such as dimethylsulfoxide, and C1–C6 dialkylamides of C1–C6 aliphatic acids, such as N,N-dimethylformamide, diethylformamide, dimethylacetamide, diethylacetamide. The carbamoylation is carried out according to conventional reaction processes between one alcohol and one isocyanate. Hence, the hydroxyl groups of hyaluronan, in its acid or salt form or in its esterified form, are reacted in a suitable solvent with the corresponding isocyanate in the presence of a Lewis base, such as a tertiary amine, or of a Lewis acid as a catalyst. The esterification is carried out by reacting the hyaluronan in its acid, salt form or, esterified form on the carboxyl group with a suitable esterifying solvent according to the methods known in the state-of-the-art. These agents are activated forms of the corresponding carboxylic acids, like anhydrides and halides. It is preferable to use bases such as tertiary amines or Lewis acids as catalysts. Several organic solvents can also be used. In some cases, specific catalysts can be used to accelerate the reaction. With this reaction, the hydroxyl groups that are carbamoylated or esterified are both the primary and the secondary hydroxyl groups.

Step b) is carried out in several stages when the primary hydroxyl groups are esterified in a different way from the secondary ones. One step entails the selective modification of the primary hydroxyl groups either of the products obtained in a) or of hyaluronan in its acid or salt form according to the process described in WO99/18133; whereas the other step entails the esterification or carbamoylation of the secondary hydroxyl groups according to the procedures described above.

In the derivatives obtained with the preparation process, the free carboxyl groups of the partially substituted polymer can possibly be salified according to the known procedures.

As starting material, hyaluronan extracted from several sources, either animal or biotechnological ones, can possibly be used. The degree of purity is not an essential feature for the preparation of the derivatives. For some specific applications, it is necessary to derivatise hyaluronan fractions with well defmed molecular weights.

When this occurs, high molecular weight hyaluronan can undergo chemical, enzymatic, chemo-enzymatic, or physical processes to obtain the desired fractions of molecular weight. The polymer to be derivatised can be obtained directly from wastes of HA (molecular weight fractions) produced for biomedical uses. These by-products can be used advantageuosly as starting material for the preparation of the derivatives of the present invention.

When the starting hyaluronan is in the form of quaternary salt, it is preferable to use the tetraalkylammonium salt, with alkyl groups from 1 to 6 carbon atoms. In most cases, hyaluronan tetrabutylammonium is used. It is possible to prepare these salts by reacting the aqueous solution of HA sodium salt or its acid form with a sulphonic resin salified with a quaternary ammonium base. Here the salt being used has the proper salinity in the organic solvents used for the derivatization.

The chemical modification of both the carboxyl and hydroxyl groups of hyaluronan to obtain the substituted derivatives of the invention leads to a dramatic reduction in the hydrophylicity of these derivatives, hence of their use in biocompatible applications. At the same time, this chemical modification allows to obtain derivatives that are soluble in a large number of organic solvents wherein the derivatives of HA known in the state-of-the-art are insoluble. As a matter of fact, it has been found that the derivatives of the invention have specific solubility properties in organic solvents. This solubility depends on the chemical nature of the substituents, the degree of substitution, the molecular weight. Depending on the degree of substitution of the hydroxyl groups, the carboxyl groups and the kind of substituent, a wide range of organic solvents can be used to solubilise the derivatives of the invention. As a matter of fact, they can be solubilised in solvents such as alcohols, ketones, esters, ethers, dialkylsulfoxides, dialkylcarboxamnides, alcohols, aliphatic or heterocyclic ketons with a low boiling point, chlorinated hydrocarbons, their mixtures. The compounds are insoluble in water, in aliphatic hydrocarbons, in dialkylethers. The solubility properties, the compatibility with specific solvents or mixtures of solvents and the stability in the presence of specific solvents or mixtures represent one peculiarity of the compounds of the invention that characterises them from the derivatives of HA known in the state of the art and that consequently allows new and peculiar uses.

The derivatives of hyaluronan of the invention can be advantageously used in the preparation of chromatographic stationary phases, including also chiral stationary phases. In fact, the applicant has surprisingly found out that the derivatives of the invention recognise specific enantiomers and allow their separation from the racemic mixtures by means of the chromatographic method.

With the aim of preparing chromatographic stationary phases, these derivatives of hyaluronan are used as such. Or else they can be used after having been ground or molded in beads and after having possibly been selected on the basis of their particle dimensions. They can alternatively be packed in a column after having been deposited on a solid support. As solid support all the supports used for chromatographic separation are suitable. They can be made up of an organic or preferably inorganic material. Examples of suitable inorganic supports are silica gel, alumina, caolin, titanium oxide, magnesium oxide, silicates and synthetic polymers. In a preferred configuration, functionalised silica is used, for example, the γ-aminopropyl-silica is used. Examples of silica gel are: Daisolgel SP-1000-7, Nucleosil 1000-7.

For this use, the suitable derivatives have a 0.1–22 dl/g intrinsic viscosity. For the derivatives of hyaluronan esterified on the carboxyl function, the 0.2–4 dl/g viscosity range is preferred. The derivatives with a lower intrinsic viscosity are not useful for the preparation of chiral stationary phases since they do not separate effectively the racemic mixtures and also because they do not have suitable reproducibility features. Moreover, some of the derivatives with a very low viscosity swell remarkably after a few separation cycles.

A group of interesting derivatives to be used in the preparation of chromatographic stationary phases is composed of derivatives with either a low or very low degree of substitution of the hydroxyl groups (0.01%–0.2%) and wherein the carboxyl groups are totally (100%) esterified. One advantage of said derivatives with a low degree or very low degree of substitution lies in the solubility properties in highly polar solvents. These compounds, when deposited on a solid support, show their unexpected efficacy in the separation of enantiomers containing polar functionalities such as the amino, hydroxyl or carboxyl groups. The surprising advantage of these derivatives consists in the possibility of preparing stationary phases that have the ability to work under reverse-phase conditions, like, for example, using water-organic solvent mixtures in whatever ratio or buffer solutions and organic solvent mixtures with defined pH values. One further advantage consists in their versatile use. As a matter of fact, they can be used not only under reverse-phase condition but also in normal phase with a single organic solvent or with mixtures of organic solvents; which entails that the operator can shift from an operation mode to the other according to the needs without decreasing the efficacy of chromatographic separation.

The chromatographic stationary phases comprising the hyaluronan derivatives of the invention constitute a further object of the present invention. These phases are prepared according to the following process. The derivatives of the invention are solubilised in a suitable solvent and the solution obtained is added to a chromatographic support. A suitable non-solvent is added to the mixture with the aim of depositing the derivative on a solid support. The material is therefore isolated, washed and dried. The modified support obtained in this way is used as a chiral stationary phase. From this stage onwards, it is clear that the solubility in a suitable solvent together with the chiroptical and enantioselective properties of the derivatives of hyaluronan are fundamental prerequisite for the production of chiral stationary phases. Other methods known to the experts can be applied on the derivatives of the invention to obtain chiral stationary phases.

These stationary-phases can be used in thin-layer chromatography, liquid chromatography, for example HPLC, batch chromatography, "simulating moving bed" (SBM) chromatography, supercritical fluid chromatography (SFC). Moreover, this invention includes a separation method of enantiomeric mixtures by means of these chiral stationary phases.

This invention moreover includes the use of these stationary phases for the separation of several racemic mixtures of commercial and industrial interest. They allow both the analytical and preparative separation of enantiomers of structurally different compounds that can also contain polar groups or that can be fully polar. Moreover, from a racemic mixture of optical isomers, it is possible, by means of the use of these stationary phases, to obtain the preparation of optically pure isomers or mixtures of isomers having an enantiomeric content higher than the one in the starting mixture. Moreover, the phases allow the determination of the enantiomeric composition of mixtures obtained for example by asymmetric synthesis. Specific examples of the separation of enantiomers by means of the stationary phases of the invention are reported in the experimental part. FIG. 1 shows the structures of the racemates tested.

Other uses of the compounds of the invention are identified on the basis of their specific solubility properties, their relative compatibility with the organic solvents and their thermal properties that distinguish them from the HA derivatives known in the state of the art. As a consequence, the compounds of this invention can be further used in the preparation of devices, such as for example, sponges, films, fibres to be used in packaging, in composite materials, in high technology materials, or else they can be used as additives for plastic materials, adhesives, varnishes. Other interesting applications concern the cosmetic field. A suitable example is provided by the preparation of hair sprays.

The following examples show the scope of invention, without having a limitative function.

EXAMPLES 1

Preparation of Benzylester of Hyaluronan 3.5 g. of tetrabutylammonium hyaluronan prepared by cationic exchange from sodium hyaluronate having viscosimetric molecular weight of 55000 (determination according to Biochimica et Biophysica Acta, 1960, 42, 476–485) are dissolved in 350 ml of N,N-dimethylformamiide in a 500 ml three-necked flask, at the temperature of 30° C., under nitrogen flux and under mechanical stirring. 8.9 mg of tetrabutylammonium iodide, 0.8 ml of triethylamine and 3.35 ml of benzylbromide are added and the reaction is carried out for 18 hours. The product is concentrated under low pressure, precipitated in 50 ml of ethylacetate; the precipitate is redissolved and riprecipitated several times, then dried and recovered. The yield is 90%. The degree of esterification, determined by means of $^1$H-NMR in DMSO at 40° C. by comparing the areas due to the methylenic protons of the benzyl (5.0–5.4 ppm) with the areas due to the methyl protons of the N-acetylamido residue (1.6–1.2 ppm) is 100%. The solubility of the derivative in N,N dimethylformamide, dimethylsulfoxide, ethylacetate, diethylether was ascertained. The derivative is soluble in N,N-dimethylformarnide, and dimethylsulfoxide.

EXAMPLE 2

Preparation of Benzylester of Hyaluronan

The procedure differs from the one described in Example 1 in that the starting sodium hyaluronan has viscosimetric molecular weight of 120000 (determination according to Biochimica et Biophysica Acta, 1960, 42, 476–485). The product has 100% degree of esterification and is determined as described in Example 1.

EXAMPLE 3

Preparation of the Benzylester of Hyaluronan 1 g of tetrabutylammonium hyaluronan prepared by cationic exchange from sodium hyaluronate having viscosimetric molecular weight of 50000 (determination according to Biochimica et Biophysica Acta, 1960, 42, 476–485) were dissolved in 100 ml of N,N-dimethylformamide in a 500 ml three-necked flask., at a temperature of 30° C., under nitrogen flux and mechanical stirring. 30 mg of tetrabutylammonium iodide, 0.22 ml of triethylamine and 0.96 ml of benzylbromide are added and the reaction is carried out for 18 hours. The product is concentrated at reduced pressure, then precipitated in 50 ml of ethylacetate, the precipitate is then redissolved and ri-precipitated several times and finally essiccated. 720 mg of product are obtained. The derivative has a degree of esterification of 100% which is determined as described in Example 1. The solubility of the derivative in solvents was tested in N,N-dimethylformamide, dimethylsulfoxide, ethylacetate, diethylether. The derivative is soluble in N,N-dimethylformamide, and dimethylsulfoxide.

EXAMPLE 4

Preparation of the Benzylester of Hyaluronan

The same procedure as in Example 3 is followed but the starting sodium hyaluronate has viscosimetric molecular weight of 18000 (determination according to Biochimica et Biophysica Acta, 1960, 42, 476–485). The product has a degree of esterification of 100% and is determined as described in Example. 1.

EXAMPLE 5

Preparation of the Benzylester of Phenylcarbamoylated Hyaluronan 1.06 g of hyaluronan benzylester of Example 2 is dispersed in 60 ml of N,N-dimethylfornamide in a 100 ml three-necked flask at the temperature of 25° C., under nitrogen flux, with a condenser and under magnetic stirring. After 1 hour, 2.5 ml of phenylisocyanate and 15 µl of dibuthyltin dilaurate are added and the reaction is carried out for 25 hours.Then, further 2.0 ml of phenylisocyanate and 10 µl of dibuthyltin dilaurate are added and the mixture is reacted for further 14 hours. The mixture is taken up to 60° C. and the mixture is reacted for further 4 hours. The solution is then concentrated at reduced pressure at about ⅕ of its volume and precipitated in 200 ml of diethylether. The solid is then filtered, washed and dried. 660 mg of product are obtained. The degree of substitution of the hydroxyl groups, as determined by means of $^1$H NMR by comparison of the areas due to the aromatic protons of the phenylcarbamate groups (6.2–7.6 ppm) with the proton areas of the polysaccharide and the benzyl methylene protons (3.0–5.2 ppm) is 100%. The intrinsic viscosity of the product is 2.06 dl/g in acetone at 20° C. The solubility of the derivatives in N,N-dimethylformamide, acetone, diethylether, and hexane was ascertained. The product is soluble in N,N-dimethylformamide and acetone.

EXAMPLE 6

Preparation of the Tetrabutylanmmonium of Phenylcarbamoylated Hyaluronan 1 g of tetrabutylammonium hyaluronan prepared by cationic exchange from sodium hyaluronate having viscosimetric molecular weight of 120,000 (determination according to Biochimica et Biophysica Acta, 1960, 42, 476–485) are dissolved in 50 ml of N,N-dimethylformamide in a 500 ml three-necked flask, at the temperature of 50° C., under nitrogen flux, with condenser and under mechanical stirring. 480 µl of 1,8-diazabicycle[ 4.5.0]undec-7-ene(1.5–5) (DBU) are added by syringe and 10 minutes after, 520 µl of phenylisocyanate diluted in 3 ml of N,N-dimethylformamide by means of a dropping funnel are added at a flux rate of 1 ml every ten minutes. The addition is repeated twice every 0.5 hours and the reaction is carried out for 0.75 hours after the last addition. The solution is concentrated under reduced pressure to about ⅓ of the volume and precipitated in 100 ml of ether. The product is dissolved in 50 ml of acetone and precipitated twice in 300 ml of ether. The precipitate is filtered and then dried. 1.2 g of product are obtained. The degree of substitution of the hydroxyl groups, as determined by means of $^1$H-NMR in DMSO at 40° C. by comparing the areas due to the aromatic protons of the phenylcarbamate groups (7.4–6.8 ppm) and the aromatic protons of the methyl group of the N-acetylamido residue (1.8–1.6 ppm) is 50%.

EXAMPLE 7

Preparation of the Tetrabutylammonium of Phenylcarbamoylated Hyaluronan 4 g of tetrabutylammonium hyaluronan prepared by cationic exchange from sodium hyaluronate having having viscosimetric molecular weight of 12000 (determination according to Biochimica et Biophysica Acta, 1960, 42, 476–485) are dissolved in 200 ml of N,N-dimethylformamide in a 500 ml three-necked flask, at the temperature of 50° C. under nitrogen flux, with condenser and under mechanical stirring. 4.8 ml of DBU are added by a syringe and, ten minutes after, 3.5 ml of phenylisocyanate diluted in 5 ml of N,N-dimethylformamide are dropped, by means of a dropping funnel, at a flux of 1 ml every 10 min. The addition is repeated 1.5 hours after and is then reacted for 1.5 hours. The solution is concentrated under reduced pressure to about ⅓ of the volume and precipitated in 200 ml ether. The product is dissolved in 200 ml acetone and precipitated twice in 1 litre of ether. The precipitate is filtered and then dried. 5 g product are obtained. The product has a degree of substitution of 100% and is determined as described in Example 6.

The intrinsic viscosity of the product is 11.5 dl/g in acetone at 20° C.

EXAMPLE 8

Preparation of the Tetrabutylammonium of Phenylcarbamoylated Hyaluronan 2g of tetrabutylammonium hyaluronan prepared by cationic exchange from sodium hyaluronate having viscosimetric molecular weight of 50000 (determination according to Biochimica et Biophysica Acta, 1960, 42, 476–485) are dissolved in 200 ml of N,N-dimethylformamide in a 500 ml three-necked flask., at a temperature of 50° C., under nitrogen flux, with condenser and under mechanical stirring. 2.4 ml of DBU are added by a syringe and, ten minutes after, 1.64 ml of phenylisocyanate diluted in 5 ml of N,N-dimethylformamide are dropped by means of a dropping funnel at a flux rate of 1 ml every 10 min. The addition is repeated twice after 1.75 hours and is then reacted for 19 hours after the last addition. The solution is concentrated under reduced pressure to about ⅓ of the volume and precipitated in 100 ml of ether. The product is dissolved in 50 ml acetone and precipitated twice in 300 ml of ether. The precipitate is filtered and then dried. 2.94 g of product are obtained. The product has 100% degree of substitution of the hydroxyl groups and is determined as described in Example 6.

EXAMPLE 9

Preparation of the Benzylester of Phenylcarbamoylated Hyaluronan 0.750 g of benzylester hyaluronan prepared as described in Example 1 are dissolved in 75 ml of N,N-dimethylformamide in a 250 ml three-necked flask, at the temperature of 50° C., under nitrogen flux, with condenser and under mechanical stirring. 50 µl of dibuthyltin dilaurate and 3.0 ml of phenylisocyanate are added by syringe and reacted for 22 hours. The product is concentrated under reduced pressure up to about ⅓ of the volume, precipitated in 200 ml of ether, then dissolved in 30 ml of acetone and finally precipitated in 200 ml of ether. The precipitate is then dissolved in 30 ml of dichloromethane and precipitated in 200 ml of methanol. The precipitate is filtered and then dried. 870 mg of product are obtained. The degree of substitution of the hydroxyl groups, determined by $^{1}$H-NMR in DMSO at 40° C. by comparing the areas due to the aromatic protons of phenyl-carbamate groups (6.2–7.6 ppm) with the areas of the protons of the polysaccharide and of the methylene of the benzyl group (3.0–5.2 ppm) is 100%. The intrinsic viscosity of the product is 0.59 dl/g in acetone at 20° C. The solubility of the derivative in N,N dimethylformamide, dimethylsulfoxide, dichloromethane, acetone, methanol, diethylether was ascertained. The derivative is soluble in N,N-dimethylformamide, dimethylsulfoxide, dichloromethane, and acetone.

EXAMPLE 10

Preparation of the Benzylester of Butyrated Hyaluronan 0.75 g of benzylester hyaluronan as described in Example 1 are dispersed in 75 ml of N,N-dimethylformamide in a 250 ml three-necked flask with a condenser, at the temperature of 50° C., under nitrogen flux and mechanical stirring. 0.74 g of dimethylaminopyridine and 1.67 ml of butyric anhydride are added by a syringe, the mixture undergoes reaction for 22 hours. The solution is concentrated under reduced pressure up to about ⅓ of the volume and is then precipitated in 150 ml ether. It is dissolved in 30 ml acetone and precipitated twice in 150 ml of ether. The precipitate is then filtered and dried. 960 mg of product are obtained. The degree of substitution of the hydroxyl groups, as determined by means of $^{1}$H-NMR in DMSO at 40° C. by comparing the areas due to the aromatic protons of the benzyl (7–7.6 ppm) with the areas due to the methyl of the butyric residue (0.8–1 ppm) is 100%. The intrinsic viscosity of the product is 0.65 dl/g in acetone at 20° C. The solubility of the derivative in N,N dimethylformamide, dimethylsulfoxide, dichloromethane, acetone, chloroform and tetrahydrofuran is ascertained. The derivative is soluble in N,N dimethylformamide, dimethylsulfoxide, dichloromethane, acetone, chloroform and tetrahydrofuran. Films are obtained by slow evaporation of both the solutions (20 mg/0.5 ml) of the derivative in dichloromethane and those of the derivative in chloroform.

EXAMPLE 11

Preparation of the Benzylester of Acetylated Hyaluronan 0.5 g of benzylester hyaluronan as described in Example 3 are dispersed in 40 ml of N,N-dimethylformamide in a 100 ml three-necked flask, at the temperature of 50° C., under nitrogen flux, with condenser and under mechanical stirring. Two hours after, the mixture is cooled down to room temperature. 50 mg of dimethylamino pyridine dissolved in 2 ml of N,N-dimethylformamide and 1.33 ml of acetic anhydride are added by a syringe and the mixture is reacted for 48 hours. The solution is concentrated under reduced pressure up to ⅓ of the volume and precipitated in 150 ml of ether. It is dissolved in 20 ml of acetone and precipitated in 150 ml of ether; this procedure is repeated twice. The precipitate is then filtered and dried. 520 mg of product are obtained. The degree of substitution of the hydroxyl groups, as determined by means of $^{1}$H-NMR in DMSO at 40° C. by comparing the areas due to the aromatic protons of the benzyl residue (7.6–7 ppm) with the areas due to the methyl protons of the acetylated residues and of the N-acetylamido residues (2.2–1.8 ppm) is 100%. The intrinsic viscosity of the product is 0.83 dl/g in acetone at 20° C.

EXAMPLE 12

Preparation of the Benzylester of Acetylated Hyaluronan

The same procedure as described in Example 11 is followed but the benzylester of Example 2 is dispersed in N,N-dimethylformamide at the temperature of 25° C. The degree of substitution of the hydroxyl groups determined by $^{1}$H-NMR as described in Example 11 is 100%. The intrinsic viscosity of the product is 1.70 dl/g in acetone at 20° C. After slow evaporation of the solvent, it is possible to prepare films from the derivative solubilised in acetone (100 mg/5ml).

EXAMPLE 13

Preparation of the Benzylester of Phenylcarbamoylated Hyaluronan 0.5 g of benzylester hyaluronan as described in Example 4 are dispersed in 100 ml of N,N-dimethylformamide in a 500 ml three-necked flask, at the temperature of 80° C., under nitrogen flux, with condenser and under mechanical stirring. Two hours after, the mixture is taken to 50° C., 15 µl of dibuthyltin dilaurate dissolved in 2 ml of N,N-dimethylformamide, and 1.75 ml of phenylsocyanate are added by a syringe and the mixture is reacted for 22 hours. The solution is concentrated under reduced pressure up to about ⅓ of the volume and precipitated in 200 ml of ether. It is then dissolved in 20 ml of acetone and precipitated in 200 ml of ether; the solid is then filtered under reduced pressure, dissolved in 20 ml of dichloromethane and precipitated in 200 ml of methanol. It is further dissolved in 20 ml of acetone and precipitated in 200 ml of ether. The precipitate is filtered and then dried. 530 mg of product are obtained. The degree of substitution of the hydroxyl groups, as determined by means of $^{1}$H-NMR by comparing the areas due to the aromatic protons of the benzyl residue (7.6–7 ppm) with the areas due to the methyl protons of the N-acetamidic residues (2.2–1.8 ppm) is 100%. The intrinsic viscosity of the product is 0.30 dl/g in acetone at 20° C. The solubility of the derivative in N,N-dimethylformamide, dimethylsulfoxide, dichloromethane, acetone, methanol, and diethylether was ascertained. The derivative is soluble in N,N-dimethylformamide, dimethylsulfoxide, dichloromethane and acetone.

EXAMPLE 14

Preparation of the Benzylester of Phenylacetylated Hyaluronan 1.0662 g of hyaluronan benzylester as described in Example 2 are dispersed in 100 ml of N,N-dimethylformamide and 20 ml of pyridine in a three-necked flask under mechanical stirring. The solution obtained in this way is laid onto a crashed ice bath and 5 ml of phenylacetylchloride are dropped onto it. The mixture is cooled down to room temperature and kept under constant stirring for 15 hours. The solution is laid onto a crashed ice bath again and further 5 ml of phenylacetylchloride are dropped onto it. The mixture is cooled down to room temperature and kept under constant stirring for three hours.

350 ml of ether are added under stirring, the precipitate is recovered by filtration, then solubilised in acetone and precipitated with methanol. The riprecipitation is repeated twice. The product is solubilised in 50 ml of methylene chloride, precipitated in 150 ml of methanol and solubilised in 200 ml of acetone, precipitated in 400 ml of water, washed and finally dried. 0.7 g of product are obtained. The degree of substitution of the hydroxyl groups, as determined by $^1$H-NMR in CDCl3 is 100%. The intrinsic viscosity of the product in acetone at 20° C. is 2.28 dl/g.

EXAMPLE 15

Preparation of the Benzylester of 3,5-dimethylphenylcarbamoylated Hyaluronan 1 g of hyaluronan benzylester obtained as described in Example 3 is dispersed in 200 ml of N,N-dimethylformamide in a 500 ml three-necked flask, at the temperature of 50° C., under nitrogen flux, with condenser and under mechanical stirring. One hour after, 15 μl of dibuthyltin dilaurate dissolved in 2 ml of N,N-dimethylformamide, and 4.5 ml of phenylisocyanate are added by a syringe and the mixture is reacted for 22 hours. The solution is concentrated under reduced pressure and precipitated in 200 ml of ether. It is dissolved in 20 ml of acetone and precipitated in 200 ml of methanol. The precipitate is then filtered and dried. 0.9 g of product are obtained. The degree of substitution of the hydroxyl groups, as determined by $^1$H-NMR by comparing the areas due to the aromatic protons of the phenylcarbamate groups (6.2–7.6 ppm) with the areas due to the protons of the polysaccharide and of the benzyl methylene (3.0–5.2 ppm), is 100%. The solubilty of the derivative was ascertained in N,N-dimethylformamide, dimethylsulfoxide, dichloromethane, acetone, and diethylether. The derivative is soluble in N,N-dimethylformamide, and dimethylsufoxide. The product obtained has 0.6 dl/g intrinsic viscosity in acetone: DMF (9:1) at 20° C.

EXAMPLE 16

Preparation of the Benzylester of Acetylated Hyaluronan 1 g of hyaluronan benzylester as described in Example 2 is dispersed in 100 ml of N-methylpyrrolidone in a 250 ml three-necked flask, at the temperature of 80° C, under nitrogen flux, with condenser and under magnetic stirring. When solubilisation is complete, the mixture is cooled down to room temperature, 4 ml of acetic anhydride and 100 mg of dimethylaminopyridine are added and the mixture is reacted for 48 hours at room temperature; The solution is then concentrated under reduced pressure up to ⅓ of its volume and precipitated in acid water. The product is then recovered by filtration and dissolved in acetone; after that, it is riprecipitated in acid water, filtered and dried in a vacuum oven at 50° C. 980 mg of product are obtained. The product has 100% degree of substitution of the hydroxyl groups and is determined as described in Example 11. The intrinsic viscosity of the product in acetone at 20° C. is 0.64 dl/g.

EXAMPLE 17

Preparation of the Methylester of Hyaluronan 500 mg of tetrabutylammonium hyaluronan prepared by cationic exchange from sodium hyaluronate having viscosimetric molecular weight of 52000 (determination according to Biochimica et Biophysica Acta, 1960, 42, 476–485) are dissolved in 100 ml of anhydrous N,N-dimethylformamide at the temperature of 50° C. under magnetic stirring in a 250 ml flask with condenser. The solution is cooled down to room temperature and then poured into a 1 litre reactor. The temperature is lowered to 4° C. and 1.5 ml of methyliodide are added; the mixture is then reacted for 48 hours under mechanical stirring. The solution is concentrated under reduced pressure up to about ⅓ of its volume and precipitated in 200 ml of diethylether. The product is washed twice in acetone, filtered and dried. 310 g of product are obtained. The derivative is characterised by $^1$H-NMR and $^{13}$C-NMR. A significant shift with respect to the starting polymer is seen, mainly of the signal due to the carboxyl on the glucuronic acid (from 167 to 171 ppm) and the two interglycosidic signals (from 81 to 83 ppm), the methyl produces a new signal at 53 ppm. The solubility of the derivative in dimethylsulfoxide, diethylether, and acetone was ascertained. The derivative is soluble in dimethylsulfoxide.

EXAMPLE 18

Preparation of the Methylester of Phenylcarbamoylated Hyaluronan 250 mg of hyaluronan methylester as described in Example 17 are dispersed in 100 ml of N,N-dimethylformamide in a 250 ml three-necked flask, at a temperature of 80° C., under nitrogen flux, with condenser and under magnetic stirring. Two hours after, the temperature is lowered to 50° C. and 1 ml of phenylisocyanate and 15 μl of dibuthyltin dilaurate are added; the mixture is reacted for 22 hours. The solution is then concentrated under reduced pressure to about ⅕ of its volume and precipitated in 200 ml of diethylether. The solid is then filtered, washed and dried. 220 mg of product are obtained. The degree of substitution as determined by $^1$H-NMR from comparison of the areas due to the aromatic protons of the phenylcarbamate groups (6.8–7.8 ppm), those due to the N-acetylamido group (1.6–2.0 ppm) and the signals due to the polysaccharide and the methyl group (2.8–5.0 ppm) is 35%. The solubility of the derivative in N,N dimethylformamide, dimethylsulfoxide, diethylether and acetone was ascertained. The product is soluble in N,N dimethylfonmamide and dimethylsulfoxide.

EXAMPLE 19

Preparation of the Benzylester of Benzoylated Hyaluronan

In a 50 ml three-necked flask supplied with a condenser, 964 mg of benzoic anhydride are poured at the temperature of 50° C. and under nitrogen flux. 100 mg of hyaluronan benzylester prepared as described in Example 4 are added in 15 ml of N,N-dimethylformamide and 32 μl of 1,8 diazabi-cyclo[5.4.0]undec-7-ene(1,5-5) (DBU) and is reacted for 22 hours. The solution is then concentrated under reduced pressure to about ⅓ of its volume and precipitated in ether. The solid is then filtered and dispersed in 100 ml of acetone that is then eliminated under reduced pressure. The product is further washed with chloroform, filtered and dried. 52 mg of product are obtained. The degree of substitution of the hydroxyl groups of the derivative as determined by $^1$H-NMR from comparison of the areas due to the aromatic protons (7.0–7.6 ppm), with that of the methylene of the benzyl (5.0–5.2 ppm) and with the signal of the N-acetylamido group (1.6 and 2.0 ppm) is to be 100%. The solubility of the derivative in N,N-dimethylformamide and dimethylsulfoxide, diethylether, acetone and chloroform was ascertained. The product is soluble in N,N-dimethylformamide and dimethylsulfoxide.

EXAMPLE 20

Preparation of the Benzylester of Hyaluronan

The same procedure as the one described in Example 3 is followed but for the viscosimetric molecular weight of the starting sodium hyaluronate which is 9000 (determination according to Biochimica et Biophysica Acta, 1960, 42, 476–485). The product has 100% degree of esterification and is determined as described in Example 1.

EXAMPLE 21

Preparation of the Allylester of Phenylcarbamoylated Hyaluronan 150 mg of tetrabutylammonium hyaluronan prepared by cationic exchange from sodium hyaluronate having viscosimetric molecular weight of 52000 (determination according to Biochimica et Biophysica Acta, 1960, 42,476–485) are dissolved in 15 ml of anhydrous N,N-dimethylformamide in a 50 ml three-necked flask at the temperature of 30° C. under nitrogen flux and magnetic stirring. When solubilisation of the polymer is completed, 200 μl of allylbromide, 40 μl of triethylamine and a catalytic amount of tetrabutylammonium iodide are added. The mixture is then reacted for 26 hours. It is then heated up to 50° C., 170 μl of phenylisocyanate are added and 10 μl of dibuthyltin dilaurate are added and the mixture is then reacted for 21 hours. The solution is then concentrated at reduced pressure up to about ⅓ of its volume and precipitated in diethylether. The solid is then filtered, washed twice in acetone and dried up. 50 mg of product are obtained. The derivative has been characterised by means of NMR ($^1$H, 2D COSY, $^1$H DOSY, $^{13}$C). From comparison of the areas due to the signals of the allylic group conjugated to hyaluronan (CH—O at 3.90 ppm, —CH= at 5.90 ppm, =CH2 from 5.22 to 5.35 ppm) with those due to the aromatic protons of the phenylcarbamate groups (from 6.8 to 7.6 ppm) and the signal of the N-acetylamido group (from 1.6 to 2.0 ppm), the degree of esterification of the carboxyl is said to be 50% and the degree of substitution of the hydroxyl groups is 100%. The solubility of the derivatives in N,N-dimethylformamide, dimethylsulfoxide, diethylether and acetone was ascertained. The product is soluble in N,N-dimethylformamide and dimethylsulfoxide.

EXAMPLE 22

Preparation of the Benzylester of Phenylcarbamoylated Hyaluronan 200 mg of hyaluronan benzylester as described in Example 3 are dispersed in 50 ml of N,N-dimethylfornamide in a 100 ml three-necked flask, at the temperature of 80° C. under nitrogen flux, with condenser and under magnetic stirring. One hour after, it is cooled down to 50° C., 15 μl of phenylisocyanate and 50 μl of dibuthyltin dilaurate are added and the mixture is reacted for 22 hours. The solution is then concentrated under reduced pressure up to about ⅕ of its volume and precipitated in 200 ml diethylether. The solid is then filtered, washed and dried. 130 mg of product were obtained. The degree of substitution of the hydroxyl groups, as determined by $^1$H NMR from comparison of the areas due to the aromatic protons (6.8–7.6 ppm), with the area due to the benzyl methylene (5.0–5.2 ppm) and the signal of the N-acetylamido group (1.6–2.0 ppm) is 2%. The solubility of the derivative in N,N-dimethylformamide and dimethylsulfoxide, diethylether and acetone was ascertained. The product is soluble in N,N-dimethylformamide and dimethylsulfoxide.

EXAMPLE 23

Preparation of the Benzylester of Phenylcarbamoylated Hyaluronan

The same procedure as the one described in Example 22 is followed but for the use of 5 μl of phenylisocyanate. The degree of substitution of the hydroxyl groups determined as described in Example 22 is 0.2%. The solubility of the derivative in N,N-dimethylformamide and dimethylsulfoxide, diethylether and acetone was ascertained. The product is soluble in N,N-dimethylformamide and dimethylsulfoxide.

EXAMPLE 24

Preparation of the Benzylester of Phenylcarbamoylated Hylauronan

The same procedure as the one described in Example 9 is followed but for the use of benzylester hyaluronan prepared as described in Example 20. The degree of substitution of the hydroxyl groups determined as described in Example 9 is 100%. The intrinsic viscosity of the product in acetone at 20° C. is 0.09 dl/g.

EXAMPLE 25

Determination of the Temperature of Glass Transition

A Differential Scanning Calorimeter (DSC) Perkin Elmer Mod. Pyris 1 previously calibrated by standard was used. 5–10 mg of the product of the invention properly laid in an aluminum cell is kept at 55° C. for 30 minutes directly in the calorimeter before each measurement. For the products described in Example 10 and Example 11 the following thermal cycles have been followed; first heating from 55° C. to 200° C. at the scanning rate of 10° C./min, subsequent cooling down to 200° C./min and second heating from 55° C. to 200° C. at 10° C./min. Both products show glass transition which occurs at the temperature (inflection point) of 130–132 ° C. for the product of Example 10 and at the temperature of 163–166° C. for the product of Example 11. For the product of Example 15 the following thermal cycles have been carried out; first heating from 55° C. to 185° C. at the scanning rate of 10° C./min, cooling down at 10° C./min, second heating from 55° C. to 185° C. at 10 C./min, cooling down at 200° C./min, third heating from from 55° C. to 185° C. at 10° C./min. The product shows glass transition at the temperature (inflection point) of 177–179° C.

EXAMPLE 26

General Procedure for the Preparation of HY Chiral Stationary Phases with the Derivatives of the Invention The derivative of the invention is solubilised in a suitable solvent by stirring it up to thorough dissolution. The solution is then filtered and added to a suspension of silica gel previously aminopropylsilanized. The system is then kept under stirring for two hours and possibly undergoes ultrasound treatment for 30 minutes. A non-solvent is added so as to lay the sample onto the silica. The precipitate is recovered and then dried. After removing the undesired particles and the solvent, the residue is dried up and the chiral stationary phase is obtained.

EXAMPLE 27

General Procedure Applied for the Separation of Racemic Mixtures by Using HPLC Columns Containing the Chiral Stationary Phases of the Invention A Knauer WellChrom Maxi-Star K-1000 pump (Knauer GmbH, Berlin, Germany) with a Knauer HPLC 6-port-valve injector and a 20 µl loop are used. The measurement is carried out at 254 nm with a Knauer WellChrom K-2500 detector. The integration of the chromatograms peaks is carried out with the BDS software package (Barspec Ltd., Rehovot, Israel). The packing of the HPLC column, bought by Max Stevenson (Berlin, Germany, 150×4.6 mm) is carried out with the "slurry" technique by using a pneumatic pump for HPLC Knauer. The analytical pure solvents by J. T. Baker used for HPLC, are redistilled before use. The dead volume of the column was measured with 1,3,5,tri-tert-buthylbenzene. The structures of the racemates tested are shown in FIG. 1.

EXAMPLE 28

Separation of Racemic Mixtures with HY-7, HY-8, HY-11

The HPLC chromatographic columns are filled with the HY-7, HY-8, and HY-11 stationary phases obtained respectively from the derivatives described in Examples 5, 9, 13. The mobile phase used for the separation of the racemates tested is n-hexane:2-propanol (9:1) at 1.0 ml/min flow rate. The chromatograms obtained allow the determination of the separation factor ($\alpha$) and the resolution factor (Rs) shown in Table 1.

TABLE 1

| | HY-7 | | HY-8 | | HY-11 | |
|---|---|---|---|---|---|---|
| Racemate | $\alpha$ | Rs | $\alpha$ | Rs | $\alpha$ | Rs |
| 2 | 1 | 0 | 1.53 | 2.87 | 1.15 | 0.62 |
| 9 | 1.53 | 0.26 | 2.40 | 7.43 | 1 | 0 |
| 10 | 1 | 0 | 1.09 | 0.37 | 1 | 0 |
| 11 | 1 | 0 | 1.17 | 0.77 | 1 | 0 |
| 12 | 1 | 0 | 2.21 | 8.25 | 1 | 0 |
| 16 | 1.44 | 0.67 | 1.98 | 1.36 | 1.29 | 0.89 |

The Table illustrates the ability of enantiorecognition of the derivatives tested and the improved ability of the HY-8 derivative.

The same racemates have been tested by using an HPLC chromatographic column filled with HY-14 obtained from the derivative of Example 24 and under the same experimental conditions. In this case no racemate is separated and the pressure in the column, which is low at the beginning, tends to increase slowly but steadily during the tests, thus indicating clearly that, under these conditions, the derivative swells.

EXAMPLE 29

Separation of Racemic Mixtures with HY-10

Racemate 12 was analysed by HPLC with a 150 mm×4.6 mm I.D. column containing the chiral stationary phase composed of the derivative of hyaluronan prepared as described in Example 11 under the following conditions: hexane/isopropanol 9:1 mobile phase; 1 ml/min flown rate. The chromatographic separation of the two enantiomers is characterised by the following parameters k'1=4.80, $\alpha$=1.32, Rs=1.36 that prove the "baseline" resolution of the racemate. After this separation, the column was used further under the following conditions: hexane/dichloromethane/methanol 68:30:2 mobile phase, 1 ml/min flow rate for 5 hours; hexane/ethylacetate 70:30 mobile phase, 1 ml/min flow rate for 5 hours; dichloromethane/ethylacetate 1:1 mobile phase, 1 ml/min flow rate for two hours. After this treatment, racemate 12 was again analysed under the initial conditions, and the baseline resolution is obtained. It is therefore clear that the chiral selector was not removed because of the changes and the kind of mobile phase used.

EXAMPLE 30

Comparison of the Separation of Racemic Mixtures with Commercial Columns

The methyl-3-hydroxy-5-oxo-1-cyclopentene-1-heptanoate racemate was analysed by means of HPLC with a 250 mm×4.6 mm I.D. column containing the chiral stationary phase based on the derivative of hyaluronan prepared as described in example 16 at the following conditions: mobile phase hexane/isopropanol 9:1; 1 ml/min flow rate. The same racemate was analysed by means of HPLC with two different commercial columns called Chiralcel OD and Chiralcel OJ, both 250 mm×4.6 mm I.D., under the same conditions. The results are reported in Table 2.

TABLE 2

| Stationary Phase | $\alpha$ | Rs |
|---|---|---|
| HY-12 | 1.21 | 1.2 |
| Chiralcel OD | 1.07 | 0.7 |
| Chiralcel OJ | 1.16 | 1.1 |

The Table shows that the stationary phase containing the derivative of the invention allows a better separation of the racemate.

EXAMPLE 31

Separation of Racemic Mixtures with HY-5 Using a Pure Solvent as a Mobile Phase

The HPLC chromatographic column is packed with HY-5 obtained with the derivate of is Example 8 and several racemic mixtures are separated. The mobile phase used is n-hexane, 1.0 ml/min flow rate. The chromatograms obtained allow the determination of the separation factor (α) and the resolution factor (Rs) shown in Table 3.

TABLE 3

| Racemate | HY-5 α | HY-5 Rs |
|---|---|---|
| 1 | 2.11 | 0.27 |
| 2 | 1.06 | 0.12 |
| 3 | 1.16 | 0.10 |
| 5 | 1.56 | 0.31 |

From the above Table it is possible to understand the enantiorecognition ability by using a pure solvent as mobile phase.

EXAMPLE 32

Separation of Racemic Mixtures (Clenbuterol, Promethazine) with HY-13 under Reverse Phase The HPLC chromatographic column is filled with the stationary phase obtained from the derivative of Example 23 and two racemic mixtures are separated. The mobile phase used is methanol: water (1:1), 1 ml/min flow rate. The two enantiomers in each mixture are resolved and the chromatograms show two separated symmetric peaks with separation factor (α) and resolution factor (Rs) shown in Table 4.

TABLE 4

| | HY-13 | |
| Racemate | α | Rs |
|---|---|---|
| Clenbuterol | 1.47 | 3.22 |
| Promethazine | 1.35 | 1.87 |

The Table shows the enantiorecognition ability of HY-13 under chromatographic reverse phase condition.

We claim:

1. Derivatives of hyaluronan, wherein the hydroxyl groups are carbamoylated in amounts ranging from 0.01% to 100% and the carboxyl groups are esterified in amounts of at least 50% with alcohols or they are in the form of salts, wherein the hydroxyl groups are carbamoylated with an isocyanate selected from the group consisting of alkyl isocyanates; alkylaryl isocyanates, and aryl isocyanate; wherein said isocyanate is optionally substituted; wherein said alkyl residue is a linear or branched, saturated or unsaturated C2–C6 alkyl, and wherein the aryl residue is mono- or polynuclear, optionally substituted with a residue selected from the group consisting of linear or branched, saturated or unsaturated C1–C5 alkyls, with halogens, nitro groups, cyano groups, and methoxy groups.

2. Derivatives according to claim 1, wherein the hydroxyl groups are carbamoylated with an isocyanate selected from the group consisting of phenylisocyanate, dialkylphenylisocyanate, trialkylphenylisocyanate and 1-phenylethylisocyanate.

3. Derivatives according to claim 1, wherein the carboxyl groups are esterified with an alcohol selected from the group consisting of aliphatic, arylaliphatic, aryl, cycloaliphatic, and heterocyclic alcohols.

4. Derivatives according to claim 1, wherein the carboxyl group is esterified with an alcohol selected from the group consisting of methylalcohol, benzylalcohol, allylalcohol, and propylalcohol.

5. Derivatives according to claim 1, wherein the hydroxyl groups are carbamoylated in amounts ranging from 0.01% to 0.2%.

6. Derivatives according to claim 1, wherein the carboxyl groups are totally esterified.

7. Derivatives according to claim 1, wherein the carboxyl groups are in the form of salt.

8. Method for the preparation of chromatographic stationary phases comprising providing a solution comprising a derivative of hyaluronan wherein the hydroxyl groups are esterified or carbamoylated in amounts ranging from 0.01% to 100%, the carboxyl groups are esterified in amounts of at least 50% with alcohols or are in the form of salts and their intrinsic viscosity ranges from 0.1 to 22 dl/g and, adding the solution to a chromatographic support.

9. Method according to claim 8 wherein said stationary phases are chiral stationary phases.

10. Chiral stationary phases comprising derivatives of hyaluronan, wherein the hydroxyl groups are esterified or carbamoylated in amounts ranging from 0.01% to 100%, the carboxylic groups esterified in amounts of at least 50% with alcohols or are in the form of salt; and the intrinsic viscosity of said derivatives ranges from 0.1 to 22 dl/g.

11. Chiral stationary phases according to claim 10, wherein the hydroxyl groups of the derivatives of hyaluronan are esterified with an acid selected from the group consisting of inorganic acids; linear or branched, saturated or unsaturated aliphatic acids; cycloaliphatic or aliphatic cycloaliphatic acids optionally polycyclic; arylaliphatic acids; aryl acids; and heterocyclic acids; wherein said acids are optionally substituted with linear or branched C1–C5 alkyl, halogens, hydroxyl groups, amino groups, nitro groups, methoxy groups, and cyano groups.

12. Chiral stationary phases according to claim 10, wherein the hydroxyl groups of the derivatives of hyaluronan are carbamoylated with an isocyanate selected from the group consisting of akyl isocyanates; alkylaryl isocyanates, and aryl isocyanates; wherein said isocyanates are optionally substituted with a residue selected from the group consisting of linear or branched C1–C5 alkyls, halogens, nitro groups, cyano groups, and methoxy groups, wherein the alkyl residue is a linear or branched, saturated or unsaturated C2–C6 alkyl and wherein the aryl residue is a mono- or polynuclear residue.

13. Chiral stationary phases according to claim 10, wherein the carboxylic groups of the derivatives of hyaluronan are esterified with an alcohol selected from the group consisting of aliphatic, arylaliphatic, aryl, cycloaliphatic, and heterocyclic alcohols.

14. Chiral stationary phases according to claim 10, wherein the hydroxyl groups of the derivatives of hyaluronan are esterified or carbamoylated in amounts ranging from 0.01% to 0.2%.

15. Chiral stationary phases according to claim 14, wherein the carboxyl groups are totally esterified.

16. Method for the preparation of optically pure isomers or of mixtures of isomers having an enantiomeric content higher than the one in a starting racemic mixture comprising providing a starting racemic mixture; and contacting the racemic mixture with a stationary phase according to claim 10.

17. Method for the preparative or analytical separation of enantiomers or mixtures of racemates comprising providing enantiomers or mixtures of racemates and contacting the enantiomers or mixtures of racemates with a stationary phase according to claim 10, in the preparative or analytical separation of enantiomers or mixtures of racemates.

18. A chromatographic method comprising contacting enantiomers or mixtures or racemates with a stationary phase according to claim 10 wherein said chromatographic method is selected from a group consisting of liquid chromatography, High Pressure Liquid Chromatography (HPLC), Simulating Moving Bed Chromatography (SMBC) and Supercritical Fluid Chromotography (SCFC).

19. Chiral stationary phases according to claim 10, where in the hydroxyl groups of the derivatives of hyaluronan are esterified or carbamoylated in amounts ranging from 70% to 100%.

20. Chiral stationary phases according to claim 19, wherein the carboxyl groups are either totally esterified or are in the form of salt.

* * * * *